United States Patent
Ishibashi et al.

(10) Patent No.: US 6,692,769 B1
(45) Date of Patent: Feb. 17, 2004

(54) SUSTAINED-RELEASE PARTICLES

(75) Inventors: Takashi Ishibashi, Sakai (JP); Keigo Nagao, Kawanishi (JP); Kengo Ikegami, Nishinomiya (JP); Hiroyuki Yoshino, Suita (JP); Masakazu Mizobe, Takatsuki (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 0 days.

(21) Appl. No.: 09/830,368

(22) PCT Filed: Oct. 22, 1999

(86) PCT No.: PCT/JP99/05834

§ 371 (c)(1),
(2), (4) Date: Apr. 26, 2001

(87) PCT Pub. No.: WO00/24423

PCT Pub. Date: May 4, 2000

(30) Foreign Application Priority Data

Oct. 26, 1998 (JP) .............................. 10/304030

(51) Int. Cl.⁷ .......................... A61K 9/14; A61K 9/20; A61K 9/22

(52) U.S. Cl. ................... 424/490; 424/464; 424/465; 424/468; 424/494; 424/495; 424/497; 424/498

(58) Field of Search ................. 424/490, 494, 424/495, 497, 498, 468, 469, 470, 464, 465

(56) References Cited

U.S. PATENT DOCUMENTS

| | | |
|---|---|---|
| 4,572,833 A | 2/1986 | Pedersen et al. |
| 4,832,955 A | 5/1989 | Snipes et al. |
| 5,445,829 A * | 8/1995 | Paradissis et al. .......... 424/480 |
| 6,087,003 A * | 7/2000 | Benoit et al. ............... 428/403 |

FOREIGN PATENT DOCUMENTS

| | | |
|---|---|---|
| EP | 0 257 310 A1 | 3/1988 |
| EP | A1263083 | 4/1988 |
| EP | 0482576 A1 | 4/1992 |
| EP | A1482576 | 4/1992 |
| EP | 0263083 A1 | 4/1998 |
| EP | 1025848 A1 | 8/2000 |
| JP | A4321621 | 11/1992 |
| JP | A04321621 | 11/1992 |
| JP | A10120571 | 5/1998 |
| JP | A11171775 | 6/1999 |

* cited by examiner

Primary Examiner—James M. Spear
(74) Attorney, Agent, or Firm—Birch, Stewart, Kolasch & Birch, LLP

(57) ABSTRACT

The present invention discloses sustained release particles having a mean particle size of 300 μm, or less, comprising a drug-containing core substance coated with a mixed coating of a hydrophobic organic compound-water-insoluble polymer, which prevents sticking during compression molding when producing oral sustained release tablets, a preparation method of those sustained release particles, and a preparation method of tablets using those sustained release particles.

18 Claims, 3 Drawing Sheets

SUSTAINED-RELEASE PARTICLES

This application is the national phase under 35 U.S.C. § 371 of PCT International Application No. PCT/JP99/05834 which has an International filing date of Oct. 22, 1999, which designated the United States of America.

TECHNICAL FIELD

The present invention relates to sustained release particles for which, together with dissolution of a drug being effectively controlled, there is no occurrence of sticking during compression, and a preparation method therefor. In addition, the present invention also relates to a preparation method for tablets using said sustained release particles.

BACKGROUND ART

An example of a known preparation method of an oral sustained release preparation is a method in which a drug-containing core substance is coated with ethyl cellulose or other water-insoluble polymer. Although this preparation has high controllability of drug release and excellent moisture resistance, humidity resistance, wear resistance, storage stability and so forth, coatings consisting only of water-insoluble polymer generally require an extremely large amount of coating to control drug release in the case of using for drugs having extremely high solubility in water or for fine particles having a mean particle size of 100 μm or less. In addition, in the case of increasing the amount of coating to delay the dissolution rate, there is the problem in which a phenomenon referred to as so-called upper limitation of dissolution occurs in which the drug does not completely dissolve.

On the other hand, Japanese Patent No. 2518882 (publication date: Jul. 31, 1996) describes a sustained release oral preparation in which pellets of inert materials are coated with a drug-containing layer, and the drug-containing layer is additionally coated with a lipophilic compound such as stearic acid and a curing agent such as ethyl cellulose. However, since the preparation described in this patent contains pellets for the core substance, the mean particle size is about 1 mm or larger. In the case of producing tablets using these large particles, disintegration of the particle-coating layer occurs easily during compression. That makes it difficult to control the dissolution of drug, or makes it necessary to increase the size of the tablets, and these shortcomings cause these particles to lack practicality as raw material particles for tablet production.

DISCLOSURE OF THE INVENTION

The present invention provides sustained release particles that prevent sticking during compression when producing oral sustained release tablets, and a preparation method and so forth thereof.

The inventors of the present invention found that, when producing sustained release tablets, if particles are used in which a drug-containing core substance is coated with a mixed coating of a hydrophobic organic compound-water-insoluble polymer, in addition to effectively controlling the dissolution of drug, sticking during compression molding is prevented thereby without adding a lubricant, and leading to completion of the present invention.

Namely, the present invention relates to sustained release particles having a mean particle size of 300 μm, or smaller, comprising a drug-containing core substance coated with a mixed coating of a hydrophobic organic compound-water-insoluble polymer, a preparation method of said sustained release particles, and a preparation method of tablets by compression using said sustained release particles.

The following provides a more detailed explanation of the present invention.

Examples of hydrophobic organic compounds used in the present invention include higher fatty acids having 6 to 22 carbons that may or may not have an unsaturated bond, higher alcohols having 6 to 22 carbons that may or may not have an unsaturated bond, and glycerin esters of higher fatty acids having 6 to 22 carbons that may or may not have an unsaturated bond.

Examples of higher fatty acids having 6 to 22 carbons that may or may not have an unsaturated bond include stearic acid, capric acid, lauric acid, myristic acid, palmitic acid, undecanoic acid, caproic acid, caprylic acid, arachidic acid, behenic acid, oleic acid, linoleic acid and linolenic acid.

Examples of higher alcohols having 6 to 22 carbons that may or may not have an unsaturated bond include lauryl alcohol, myristyl alcohol, cetyl alcohol, stearyl alcohol and undecanol.

Examples of glycerin esters of higher fatty acids having 6 to 22 carbons that may or may not have an unsaturated bond include glycerin esters of the above higher fatty acids such as stearin, myristin, palmitin and laurin.

Of these, higher fatty acids having 6 to 22 carbons that may or may not have an unsaturated bond are preferable, and stearic acid is particularly preferable.

Not only one types of the above hydrophobic organic compounds, but also a mixture of two or more types may be used for the hydrophobic organic compound.

In addition, examples of water-insoluble polymer used in the present invention include water-insoluble cellulose derivatives, water-insoluble vinyl derivatives and water-insoluble insoluble acrylic polymers.

Specific examples of the above water-insoluble cellulose derivatives include ethyl cellulose and cellulose acetate.

Specific examples of water-insoluble vinyl derivatives include polyvinyl acetate and polyvinyl chloride.

Specific examples of water-insoluble acrylic polymers include ethyl acrylate-methyl methacrylate-trimethylammoniumethyl methacrylate chloride copolymer and methyl methacrylate-ethyl acrylate copolymer.

Of these, water-insoluble cellulose derivatives are preferable, and ethyl cellulose is particularly preferable.

Not only one type of the above water-insoluble polymers, but also a mixture of two or more types may be used for the water-insoluble polymer.

In the mixed coating of a hydrophobic organic compound-water-insoluble polymer, hydrophobic organic compound and water-insoluble polymer can be used by suitably combining each of the above coating agents, and mixtures of one type or two or more types of hydrophobic organic compounds, or mixtures of one type or two or more types of water-insoluble polymers can be used in combination. Of these, a preferable combination is higher fatty acid having 6 to 22 carbons that may or may not contain an unsaturated bond and a water-insoluble cellulose derivative, while a particularly preferable combination is stearic acid and ethyl cellulose.

In the mixed coating as claimed in the present invention, the mixing ratio of hydrophobic organic compound and water-insoluble polymer and the coating ratio of the mixed coating is suitably determined according to the effective dose, and so forth, of the drug used. In this case, the higher the ratio of hydrophobic organic compound to water-insoluble polymer in the mixed coating, the easier it is to control dissolution time. In addition, the greater the coating ratio of the mixed coating to the drug containing core substance, the easier it is to control dissolution time.

The mixing ratio of hydrophobic organic compound and water-insoluble polymer in the mixed coating is normally within the range of 5:95 to 95:5, and particularly preferably within the range of 30:70 to 80:20.

In addition, although the coated amount of mixed coating fluctuates according to the type and size of the core substance, the coating ratio (wt % of mixed coating to core substance) should be within the range of 20 to 200 wt %, and particularly preferably within the range of 40 to 100 wt %.

Moreover, various additives may be blended into the mixed coating as claimed in the present invention, and examples of such additives include colorants, opacifiers, plasticizers and lubricants.

Examples of colorants include food dyes, lake pigment, caramel, carotene, annato, cochenille and iron oxide, as well as opaque colorants consisting mainly of lake pigment and syrup (OPALUX). Specific examples of these colorants include aluminum lake food dyes such as red food dye No. 2 and No. 3, yellow dye No. 4 and No. 5, green dye No. 3, blue dye No. 1 and No. 2 and violet dye No. 1, annato (natural pigment originating in Bixa orellana), carmine (aluminum carminate), and pearl essence (consisting mainly of guanine).

Examples of opacifiers include titanium dioxide, precipitated calcium carbonate, calcium hydrogenphosphate and calcium sulfate.

Examples of plasticizers include phthalic acid derivatives such as ethyl phthalate, dibutyl phthalate and butylphthalyl butylglycolate, as well as silicon oil, triethyl citrate, triacetin, propylene glycol and polyethylene glycol.

Examples of lubricants include magnesium stearate, talc, synthetic magnesium silicate and finely particulate silicon oxide.

The added amounts and addition timing of these additives are suitably selected on the basis of information conventionally used in the field of pharmaceutical technology.

The sustained release particles of the present invention can be easily produced by spray-coating with a coating solution, consisting of a hydrophobic organic compound and a water-insoluble polymer dissolved in a solvent, onto a drug-containing core substance.

The solvent of the coating solution may be any solvent that dissolves both the above hydrophobic organic compound and water-insoluble polymer, examples of which include alcohols such as methanol, ethanol, n-propanol, isopropanol, n-butanol, 2-methoxyethanol (trade name: Methylcellosorve, Katayama Chemical Ind.) and 2-ethoxyethanol (trade name: is Cellosorve, Katayama Chemical Ind.), hydrocarbons such as hexane, cyclohexane, petroleum ether, petroleum benzene, ligroin, benzene, toluene and xylene, ketones such as acetone and methyl ethyl ketone, halogenated hydrocarbons such as dichloromethane, chloroform, carbon tetrachloride, ethylene dichloride, trichloroethylene and 1,1,1-trichloroethane, esters such as methyl acetate ester, ethyl acetate ester and butyl acetate ester, and ethers such as isopropyl ether and dioxane.

These solvents should be selected according to the hydrophobic organic compound and water-insoluble polymer used, and two or more types can be used after suitably lending. Particularly preferable solvents are alcohols, and the most preferable is ethanol.

Coating should be performed using a known coating apparatus, examples of which include a fluidized bed coating apparatus, centrifugal fluidized bed coating apparatus and pan coating apparatus.

The drug-containing core substance as claimed in the present invention may be composed of drug only, or may be composed of a drug and various types of preparation additives normally used in this field.

The mean particle size of the drug-containing core substance is within the range of 40–200 nm, and preferably within the range of 60–150 nm.

There are no particular restrictions on the drug provided it can be administered orally, and various examples of such drugs are as follows: (1) antipyretics, analgesics and antiphlogistics (such as indometacin, aspirin, diclofenac sodium, ketoprofen, ibuprofen, mefenamic acid, azulene, phenacetin, isopropyl antipyrine, acetaminophen, benzadac, phenylbutazone, flufenamic acid, sodium salicylate, salicylamide, sazapyrine and etodolac), (2) steroid anti-inflammatory drugs (such as dexamethasone, hydrocortisone, prednisolone and triamcinolone), (3) anti-ulcer drugs (such as ecabet sodium, enprostil, sulpiride, cetraxate hydrochloride, gefarnate, irsogladine maleate, cimetidine, ranitidine hydrochloride, famotidine, nizatidine and roxatidine acetate hydrochloride), (4) coronary vasodilators (such as nifedipine, isosorbide dinitrate, diltiazem hydrochloride, trapidil, dipyridamole, dilazep hydrochloride, verapamil, nicardipine, nicardipine hydrochloride and verapamil hydrochloride), (5) peripheral vasodilators (such as ifenprodil tartrate, cinepacide maleate, ciclandelate, cynnaridine and pentoxyfylline), (6) antibiotics (such as ampicillin, amoxicillin, cefalexin, erythromycin ethyl succinate, bacampicillin hydrochloride, minocycline hydrochloride, chloramphenicol, tetracycline, erythromycin, ceftazidime, cefuroxime sodium, aspoxicillin and ritipenem acoxyl hydrate), (7) synthetic antimicrobials (such as nalidixic acid, piromidic acid, pipemidic acid trihydrate, enoxacin, cinoxacin, ofloxacin, norfloxacin, ciprofloxacin hydrochloride and sulfamethoxazole-trimethoprim), (8) antiviral agents (such as aciclovir and ganciclovir), (9) anticonvulsants (such as propantheline bromide, atropine sulfate, oxitropium bromide, timepidium bromide, scopolamine butylbromide, trospium chloride, butropium bromide, N-methylscopolamine methylsulfate and methyloctatropine bromide), (10) antitussives (such as tipepidine hibenzate, methylephedrine hydrochloride, codeine phosphate, tranilast, dextromethorphan hydrobromide, dimemorfan phosphate, clofenadol hydrochloride, fominoben hydrochloride, benproperine phosphate, eprazinone hydrochloride, clofedanol hydrochloride, ephedrine hydrochloride, noscapine, pentoxyverine citrate, oxeladin citrate and isoaminyl citrate), (11) expectorants (such as bromhexine hydrochloride, carbocysteine, ethyl cysteine hydrochloride and methylcysteine hydrochloride), (12) bronchodilators (such as theophylline, aminophylline, sodium cromoglicate, procaterol hydrochloride, trimetoquinol hydrochloride, diprophylline, salbutamol sulfate, clorprenaline hydrochloride, formoterol fumarate, orciprenaline sulfate, pirbuterol hydrochloride, hexoprenaline sulfate, bitolterol mesilate, clenbuterol hydrochloride, terbutaline sulfate, mabuterol hydrochloride, fenoterol hydrobromide and methoxyphenamine hydrochloride), (13) cardiacs (such as dopamine hydrochloride, dobutamine hydrochloride, docarpamine, denopamine, caffeine, digoxin, digitoxin and ubidecarenone), (14) diuretics (such as furosemide, acetazolamide, trichlormethiazide, methylclothiazide, hydrochlorothiazide, hydroflumethiazide, ethiazide, cyclopenthiazide, spironolactone, triamterene, florothiazide, piretanide, mefruside, etacrynic acid, azosemide and clofenamide), (15) muscle relaxants (such as chlorphenesin carbamate, tolperisone hydrochloride, eperisone hydrochloride, tizanidine hydrochloride, mephenesine, chlorzoxazone, phenprobamate, methocarbamol, chlormezanone, pridinol mesilate, afloqualone, baclofen and dantrolene sodium), (16) cerebral metabolism ameliorants (such as nicergoline, meclofenoxate hydrochloride and taltireline), (17) minor tranquilizers (such as oxazolam, diazepam, clotiazepam, medazepam, temazepam, fludiazepam, meprobamate, nitrazepam and chlordiazepoxide), (18) major tranquilizers (such as sulpiride, clocapramine hydrochloride, zotepine, chlorpromazine and haloperidol), (19) β-blockers (such as bisoprolol fumarate, pindolol, propranolol hydrochloride, carteolol hydrochloride, metoprolol tartrate, labetanol hydrochloride, acebutolol hydrochloride, bufetolol hydrochloride, alprenolol hydrochloride, arotinolol hydrochloride, oxprenolol hydrochloride, nadolol, bucumolol hydrochloride, indenolol hydrochloride, timolol maleate, befunolol hydrochloride and bupranolol hydrochloride), (20) antiarrthymics (such as procainamide hydrochloride, disopyramide phosphate, cibenzoline succinate, ajmaline, quinidine sulfate, aprindine hydrochloride, propafenone hydrochloride, mexiletine hydrochloride and ajmilide hydrochloride), (21) athrifuges (such as allopurinol, probenicid, colistin, sulfinpyrazone, benzbromarone and bucolome), (22) anticoagulants (such as ticlopidine hydrochloride, dicumarol, potassium warfarin, and (2R,3R)-3-acetoxy-5-[2(dimethylamino)ethyl]-2,3-dihydro-8-methyl-2-(4-ethylphenyl)-1,5-benzothiazepine-4(5H)-one maleate), (23) thrombolytics (such as methyl(2E,3Z)-3-benzylidene-4-(3,5-dimethoxy-α-methyl benzylidene)-N-(4-methylpiperazin-1-yl) succinamate hydrochloride), (24) liver disease drugs (such as (±)r-5-hydroxymethyl-t-7-(3,4-dimethoxyphenyl)-4-oxo-4,5,6,7-tetrahydrobenzo [b]furan-c-6-carboxylactone), (25) antiepileptics (such as phenytoin, sodium valproate, metalbital and carbamazepine), (26) antihistamines (such as chlorpheniramine maleate, clemastine fumarate, mequitazine, alimemazine tartrate, cyproheptadine hydrochloride and bepotastin besilate), (27) antiemitics (such as difenidol hydrochloride, metoclopramide, domperidone and betahistine mesilate and trimebutine maleate), (28) depressors (such as dimethylaminoethyl reserpilinate dihydrochloride, rescinnamine, methyldopa, prazocin hydrochloride, bunazosin hydrochloride, clonidine hydrochloride, budralazine, urapidil and N-[6-[2-[(5-bromo-2-pyrimidinyl)oxy] ethoxy]-5-(4-methylphenyl)-4-pyrimidinyl]-4-(2-hydroxy-1,1-dimethylethyl)benzene sulfonamide sodium), (29) hyperlipidemia agents (such as pravastatin sodium and fluvastatin sodium), (30) sympathetic nervous stimulants (such as dihydroergotamine mesilate and isoproterenol hydrochloride, etilefrine hydrochloride), (31) oral diabetes therapeutic drugs (such as glibenclamide, tolbutamide and glymidine sodium), (32) oral carcinostatics such as marimastat), (33) alkaloid narcotics (such as orphine, codeine and cocaine), (34) vitamins (such as itamin B1, vitamin B2, vitamin B6, vitamin B12, vitamin C and folic acid), (35) thamuria therapeutic drugs (such as flavoxate hydrochloride, oxybutynin hydrochloride and terolidine hydrochloride), and (36) angiotensin convertase inhibitors (such as imidapril hydrochloride, enalapril maleate, alacepril and delapril hydrochloride).

There are no particular restrictions on preparation additives used as the above core substance, and all such additives that can be used in the form of solid preparations can be used preferably. Examples of such additives include excipients such as lactose, sucrose, mannitol, xylitol, erythritol, sorbitol, maltitol, calcium citrate, calcium phosphate and crystalline cellulose, disintegrating agents such as cornstarch, potato starch, sodium carboxymethyl cellulose, partially pregelatinised starch, calcium carboxymethyl cellulose, carboxymethyl cellulose, lowly-substituted hydroxypropyl cellulose, crosslinked sodium carboxymethyl cellulose and crosslinked polyvinyl pyrrolidone, binders such as hydroxypropyl cellulose, hydroxypropyl methyl cellulose, polyvinyl pyrrolidone, polyethylene glycol, dextrin and pregelatinised starch, lubricants such as magnesium stearate, calcium stearate, talc, light anhydrous silicic acid and hydrated silicon dioxide, surfactants such as phospholipids, glycerin fatty acid esters, sorbitan fatty acid esters, polyoxyethylene fatty acid esters, polyethylene glycol fatty acid esters, polyoxyethylene hydrogenated castor oil, polyoxyethylene alkyl ether and sucrose fatty acid esters, fragrances such as orange and strawberry, colorants such as iron sesquioxide, yellow iron sesquioxide, yellow food dye No. 5, yellow food dye No. 4 and aluminum lake, sweeteners such as saccharin and asparteme, correctives such as citric acid, sodium citrate, succinic acid, tartaric acid, fumaric acid and glutamic acid, and solubilizers such as cyclodextrin, arginine, lysine and tris-aminomethane.

The drug-containing core substance can be prepared according to known granulation methods such as wet granulation and dry granulation.

When using wet granulation, after mixing the drug and each preparation additive in accordance with conventional methods, a binder solution is added followed by granulation with a stirring granulating machine or high-speed stirring granulating machine, or after adding a binder solution to a mixture of drug and various preparation additives and kneading, granulation and grading should be performed using an extrusion granulating machine. In addition, a mixture of drug and various preparation additives may also be granulated by spraying a binder solution onto a fluidized bed using a fluidized bed granulator, rolling stirring fluidized bed granulator and so forth.

When using dry granulation, a mixture of drug and various preparation additives should be granulated using a roller compacter and roll granulator, etc.

In the sustained release particles of the present invention, in order to prevent interaction between drug-containing core substance and mixed coating component, or to adjust the drug dissolution rate, a layer such as a water-soluble substance, water-insoluble substance or gastrolytic substance may be provided between the core substance and mixed coating of hydrophobic organic compound-water-insoluble polymer.

Examples of said water-soluble substances include water-soluble cellulose ethers such as methyl cellulose, hydroxypropyl cellulose and hydroxypropyl methyl cellulose, water-soluble polyvinyl derivatives such as polyvinyl pyrrolidone and polyvinyl alcohol, and alkylene oxide polymers such as polyethylene glycol. Examples of water-insoluble substances include water-insoluble cellulose ethers such as ethyl cellulose, water-insoluble acrylic acid copolymers such as ethyl acrylate-methyl methacrylate-trimethylammoniumethyl methacrylate chloride copolymer (e.g., trade name: Eudragit RS, Rohm Pharma.) and methyl methacrylate-ethyl acrylate copolymer (e.g., trade name: Eudragit NE30D, Rohm Pharma.), and hydrogenated oil. Examples of gastrolytic substances include gastrolytic polyvinyl derivatives such as polyvinyl acetal diethyl aminoacetate, and gastrolytic acrylic acid copolymers such as methylmethacrylate-butylmethacrylate-dimethylaminoethyl methacrylate copolymer (e.g., trade name: Eudragit E, Röhm Pharma.).

The sustained release particles of the present invention are targeted at those having a mean particle size of 300 μm, those having a particle size of 50–250 μm are preferable, and those having a particle size of 75–150 μm are particularly preferable.

In the case of a person with ordinary skill in the art, a mixing ratio and coated amount so as to obtain the desired dissolution rate can be easily determined by preparing preparations comprised of various mixing ratios and coated amounts in order to produce the sustained release particles of the present invention.

Although the sustained release particles of the present invention can be used as an orally administered preparation, they can also be used as raw material particles for tablets, and after adding various additives as necessary, can be used to produce the tablets of the present invention by compression molding in accordance with conventional methods.

The tablets of the present invention can be produced by compression molding in accordance with conventional methods using sustained release particles having a mean particle size of 300 μm or less obtained in the manner described above. More specifically, after producing in advance granules for compression by mixing or kneading excipient (e.g., mannitol, crystal cellulose, lactose, sucrose, calcium phosphate or calcium citrate) and binder (e.g., polyvinyl pyrrolidone, hydroxylpropyl methyl cellulose, hydroxypropyl cellulose or dextrin), the tablets can be produced using, for example, a rotary tabletting machine. Tabletting can be preferably carried out under normal conditions of 10–50 rpm for the tabletting speed. In addition, the pressure used for tabletting is preferably set within the range of a conventional tabletting pressure of 200–1100 kg/punch.

The resulting compressed preparation may be in the form of coated tablets by sugar-coating or film-coating as desired. Said coating can be carried out in accordance with conventional methods for all types of coatings.

BEST MODE FOR CARRYING OUT THE INVENTION

Figure 1:
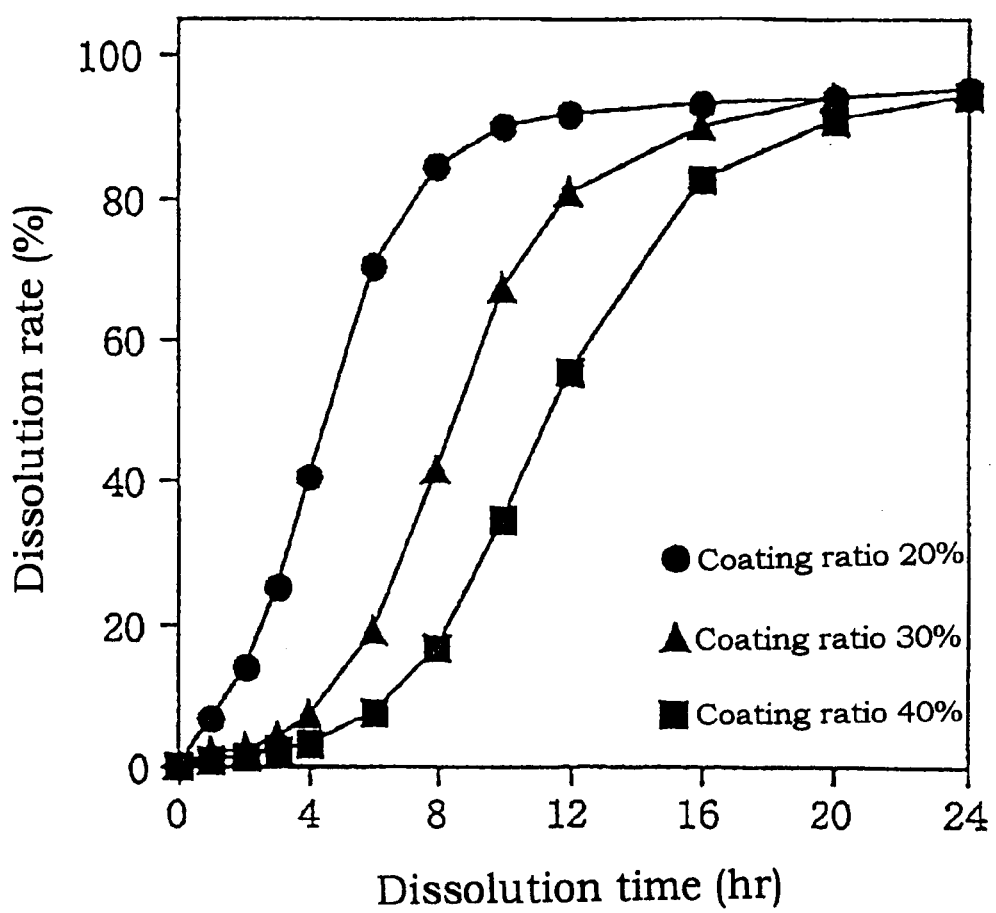
FIG. 1 is a graph showing the behavior of the dissolution of diltiazem hydrochloride from sustained release particles coated with ethyl cellulose-stearic acid=1:1 in 2nd fluid.

Although the following provides a detailed explanation of the present invention using comparative examples and examples, the present invention is not limited to these.

EXAMPLE 1

(1) Preparation of Core Particles

Using a stirring granulating machine (Powrex), 100 g of diltiazem hydrochloride, 50 g of mannitol and 50 g of crystalline cellulose (Grade: PH-M25, Asahi Chemical Industry) were granulated with adding 400 g of an aqueous ethanol (ethanol content: 80 wt %) in which 4 g of hydroxypropyl cellulose (Grade: HPC-SL, Shin-Etsu Chemical) were dissolved. After drying, the particles were graded to obtain core particles having a mean particle size of 79 μm.

(2) Preparation of Sustained Release Particles

Three types of granules having different coating amounts were obtained that were coated with ethyl cellulose and stearic acid by coating 100 g of the resulting core granules with a solution in which 25 g of ethylcellulose (Grade: #10, Dow Chemical) and 25 g of stearic acid were dissolved in 1000 g of ethanol using a Wurster type fluidized bed granulation coating apparatus (Model GPCC-1, Glatt) so that the coating ratios on the core particles were 20 wt %, 30 wt % or 40 wt %. The mean particle size of each of these particles was 300 μm or less.

(3) Dissolution Test

Dissolution tests were performed on the particles obtained above under conditions of 37° C. and paddle rotating speed of 100 rpm using 900 ml of the 2nd fluid for disintegration test of Japanese Pharmacopeia (JP) (pH 6.8) in accordance with the dissolution test (paddle method) of the 13th Revision of the JP. Those results are shown in FIG. 1.

(4) Results and Discussion

The dissolution behavior of the above three types of preparations are as shown in FIG. 1. For example, the 50% dissolution time of coated particles on which the coating ratio was 40 wt % was 11.7 hours, indicating that the dissolution rate is sufficiently suppressed. Moreover, there was hardly any upper limitation of dissolution phenomenon observed. In addition, there was hardly any generation of static electricity during coating of the coating layer, and adhesion of the particles to the apparatus and equipment was hardly observed at all. Moreover, there was little aggregation between particles during coating and, for example, in the case of coated particles the coating ratio of which was 40 wt %, the mean particle size of the resulting sustained release particles was 116 μm, and the distribution of particles of 80 mesh or more was only 8.3%.

EXAMPLE 2

(1) Preparation of Sustained Release Particles

Three types of particles coated with ethyl cellulose and stearic acid but having different coating amounts were obtained by coating core particles so that the coating ratios were 30 wt %, 60 wt % or 80 wt % by treating in the same manner as (1) and (2) of Example 1 with the exception of using a solution in which 80 g of ethyl cellulose (Grade: #10, Dow Chemical) and 20 g of stearic acid were dissolved in 2000 g of ethanol. The mean particle size of each of these particles was 300 μm or less.

(2) Results of Dissolution Test and Discussion

Figure 2:
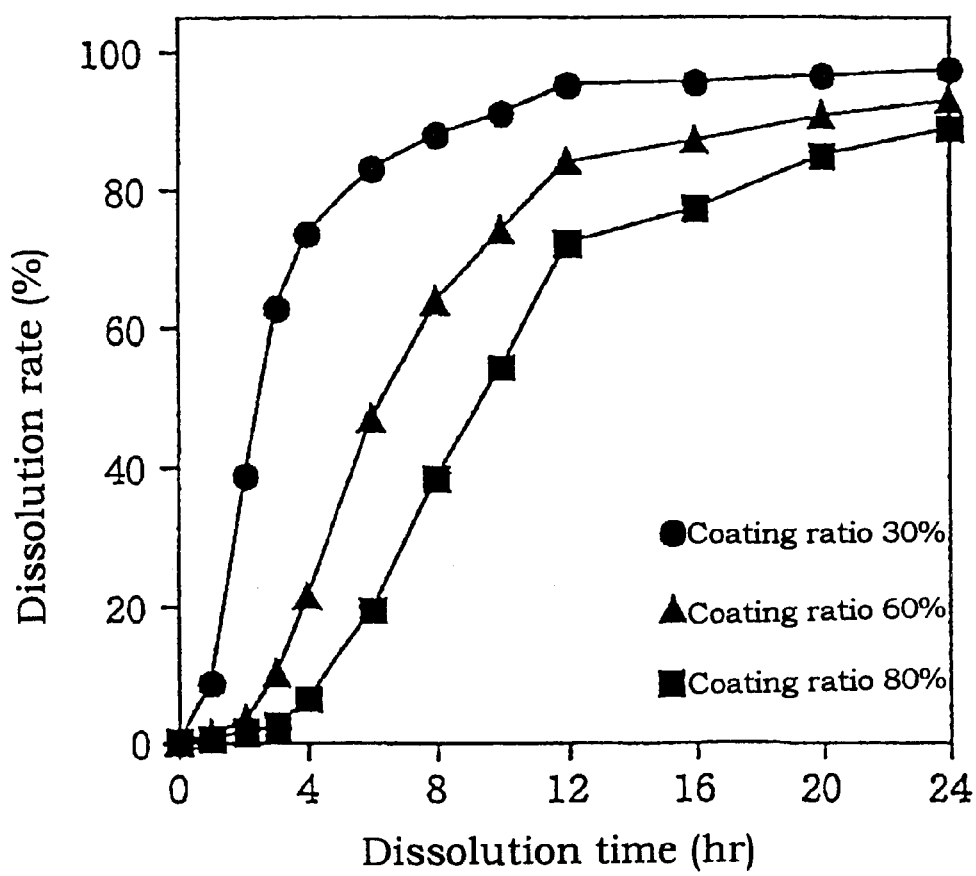
FIG. 2 is a graph showing the behavior of dissolution of diltiazem hydrochloride from sustained release particles coated with ethyl cellulose-stearic acid=4:1 in 2nd fluid.

The results of performing dissolution tests in the same manner as (3) of Example 1 are shown in FIG. 2. For example, the 50% dissolution time in particles coated so that the coating ratio of the core particles was 80 wt % was 9.5 hours, indicating that the dissolution rate was sufficiently suppressed. Moreover, the dissolved amount after 24 hours was 92%, and hardly any upper limitation of dissolution phenomenon was observed. In addition, there was hardly any generation of static electricity during coating of the coating layer, and adhesion of the particles to the apparatus and equipment was hardly observed at all.

EXAMPLE 3

(Preparation of Tablets Containing Sustained Release Particles)

300 g of mannitol and 18 g of polyvinyl pyrrolidone (Grade: #30, BASF) were kneaded and granulated using a Shinagawa mixer (Shinagawa Industries). After grading the resulting granulation product with a 12 mesh and 24 mesh sieve, the granules were dried to obtain 30 g of granules for compression.

150 g of the particles obtained in Example 1 were mixed with 225 g of the above granules for compression, and as a result of compression at a tabletting speed of 25 rpm and tabletting pressure of 400 kg/punch using a rotary tabletting machine (Model F-9, Kikusui Seisakusho), tablets containing 375 mg of sustained release particles per tablet having a diameter of 16 mm were obtained without the occurrence of sticking.

Comparative Example 1

Figure 3:
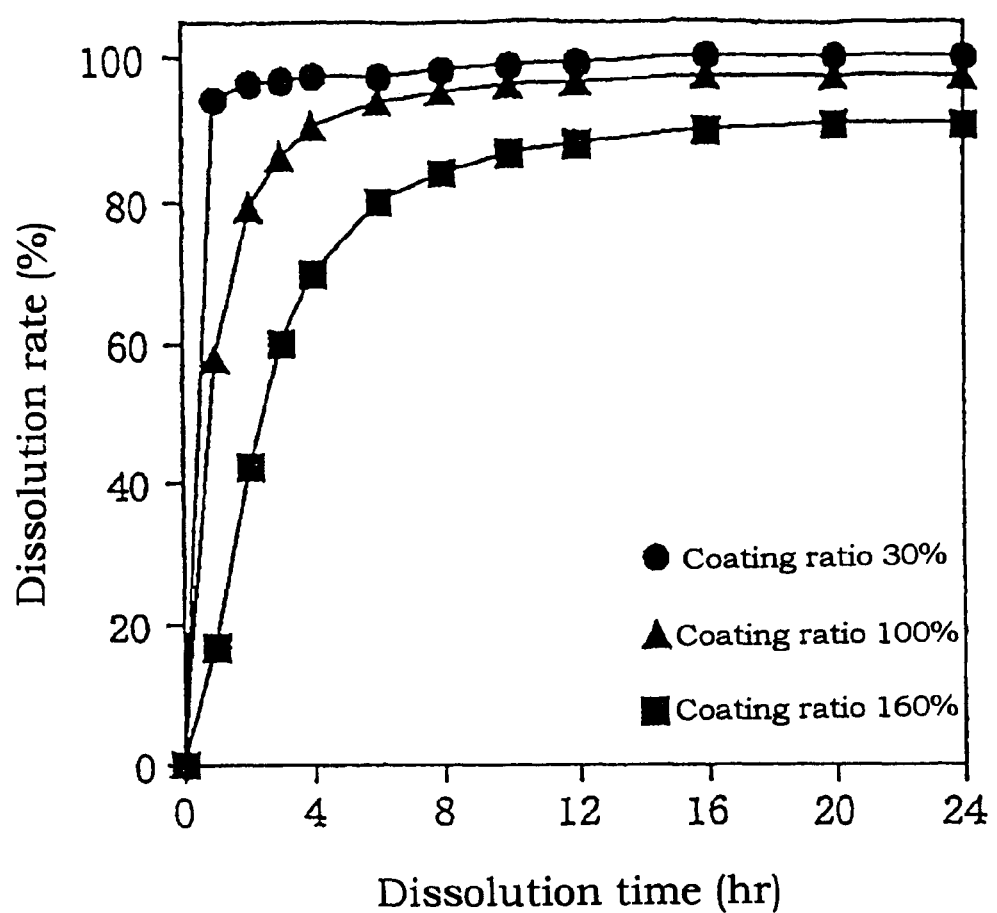
FIG. 3 is a graph showing the behavior of dissolution of diltiazem hydrochloride from ethyl cellulose coated particles in 2nd fluid.

(1) Three types of particles coated with ethyl cellulose but having different coating ratios were obtained by coating 100 g of core particles obtained in (1) of Example 1 using a Wurster-type fluidized bed granulation coating apparatus (Model GPCC-1, Glatt) with a solution in which 200 g of ethyl cellulose (Grade: #10, Dow Chemical) were dissolved in 4000 g of ethanol at a coating ratio relative to the core particles of 30 wt %, 100 wt % or 160 wt %.
(2) Results of Dissolution Tests and Discussion The results of performing dissolution tests in the same manner as (3) of Example 1 are as shown in FIG. 3. For example, the 50% dissolution time even in particles coated so that the coating ratio relative to the core particles was 160 wt % was 2.3 hours, thus indicating that dissolution rate was unable to be sufficiently suppressed. In addition, remarkably powerful static electricity was generated during coating of the coating layer, and particles were observed to adhere to the apparatus and equipment.

Moreover, prominent aggregation was observed between particles during coating and for example, in particles coated to have a coating ratio of 30 wt %, the mean particle size of the resulting sustained release particles was 137 μm, and the distribution of particles of 80 mesh or larger was 21.7%.

INDUSTRIAL APPLICABILITY

The sustained release particles of the present invention are able to extremely efficiently control dissolution of drug. In addition, since static electricity is not generated during production of the sustained release particles of the present invention, adherence of particles to the walls of the production equipment and aggregation between particles can be prevented. Moreover, since there is no occurrence of sticking during production of tablets by forming the sustained release particles of the present invention into tablets, the present invention also offers the advantage of not requiring the addition of lubricant.

What is claimed is:

1. Sustained release particles having a mean particle size of 300 μm or less comprising: a drug-containing core substance coated with mixed coating of a hydrophobic organic compound-water-insoluble polymer.

2. The sustained release particles according to claim 1 wherein, the hydrophobic organic compound is one type or two or more types selected from the group consisting of higher fatty acids having 6 to 22 carbons that may or may not have an unsaturated bond, higher alcohols having 6 to 22 carbons that may or may not have an unsaturated bond, and glycerin esters of higher fatty acids having 6 to 22 carbons that may or may not have an unsaturated bond; and, said water-insoluble polymer is one type or two or more types selected-from the group consisting of water-insoluble cellulose derivatives, water-insoluble vinyl derivatives and water-insoluble acrylic polymers.

3. The sustained release particles according to claim 2 wherein, higher fatty acid having 6 to 22 carbons that may or may not have an unsaturated bond is stearic acid, capric acid, lauric acid, myristic acid, palmitic acid, undecanoic acid, caproic acid, caprylic acid, arachidic acid, behenic acid, oleic acid, linoleic acid or linolenic acid, higher alcohol having 6 to 22 carbons that may or may not have an unsaturated bond is lauryl alcohol, myristyl alcohol, cetyl alcohol, stearyl alcohol or undecanol, glycerin ester of a higher fatty acid having 6 to 22 carbons that may or may not have an unsaturated bond is stearin, myristin, palmitin or laurin, water-insoluble cellulose derivative is ethyl cellulose or cellulose acetate, water-insoluble vinyl derivative is polyvinyl acetate or polyvinyl chloride, and water-insoluble acrylic polymer is ethyl acrylate-methyl methacrylate-trimethylammoniumethyl methacrylate chloride copolymer or methyl methacrylate-ethyl acrylate copolymer.

4. The sustained release particles according to claim 1 wherein, the hydrophobic organic compound is stearic acid, and the water-insoluble polymer is ethyl cellulose.

5. The sustained release particles according to any one of claims 1 to 4 wherein, the mixing ratio of hydrophobic organic compound and water-insoluble polymer in mixed coating of the hydrophobic organic compound-water-insoluble polymer is within the range of 5:95 to 95:5.

6. The sustained release particles according to claim 1 wherein, the coating rate of mixed coating of the hydrophobic organic compound-water-insoluble polymer is within the range of 20 to 200 wt %.

7. The sustained release particles according to claim 1 that are raw material particles for tablets.

8. A preparation method of sustained release particles having a mean particle size of 300 μm or less comprising: spray-coating with a solution containing a hydrophobic organic compound-water-insoluble polymer mixture onto a drug-containing core substance.

9. The preparation method of sustained release particles according to claim 8 wherein, the hydrophobic organic compound is one type or two or more types selected from the group consisting of higher fatty acids having 6 to 22 carbons that may or may not have an unsaturated bond, higher alcohols having 6 to 22 carbons that may or may not have an unsaturated bond, and glycerin esters of higher fatty acids having 6 to 22 carbons that may or may not have an unsaturated bond; and, said water-insoluble polymer is one type or two or more types selected from the group consisting of water-insoluble cellulose derivatives, water-insoluble vinyl derivatives and water-insoluble acrylic polymers.

10. A preparation method of tablets comprising: spray-coating with a solution containing a hydrophobic organic compound-water-insoluble polymer mixture onto a drug-containing core substance, and compression using the resulting sustained release particles having a mean particle size of 300 μm or less.

11. The preparation method of tablets according to claim 10 wherein, the hydrophobic organic compound is one type or two or more types selected from the group consisting of higher fatty acids having 6 to 22 carbons that may or may not have an unsaturated bond, higher alcohols having 6 to 22 carbons that may or may not have an unsaturated bond, and glycerin esters of higher fatty acids having 6 to 22 carbons that may or may not have an unsaturated bond; and, said water-insoluble polymer is one type or two or more types selected from the group consisting of water-insoluble cellulose derivatives, water-insoluble vinyl derivatives and water-insoluble acrylic polymers.

12. Sustained release particles having a mean particle size of 300 μm or less comprising: a drug-containing core substance spray-coated with mixed coating of a hydrophobic organic compound-water-insoluble polymer.

13. The sustained release particles according to claim 12 wherein, the hydrophobic organic compound is one type or two or more types selected from the group consisting of higher fatty acids having 6 to 22 carbons that may or may not have an unsaturated bond, higher alcohols having 6 to 22 carbons that may or may not have a unsaturated bond, and glycerin esters of higher fatty acids having 6 to 22 carbons that may or may not have an unsaturated bond; and, said water-insoluble polymer is one type or two or more types selected from the group consisting of water-insoluble cellulose derivatives, water-insoluble vinyl derivatives and water-insoluble acrylic polymers.

14. The sustained release particles according to claim 13 wherein, higher fatty acid having 6 to 22 carbons that may or may not have an unsaturated bond is stearic acid, capric acid, lauric acid, myristic acid, palmitic acid, undecanoic acid, caproic acid, caprylic acid, arachidic acid, behenic acid, oleic acid, linoleic acid or linolenic acid, higher alcohol having 6 to 22 carbons that may or may not have an unsaturated bond is lauryl alcohol, myristyl alcohol, cetyl alcohol, stearyl alcohol or undecanol, glycerin ester of a higher fatty acid having 6 to 22 carbons that may or may not have an unsaturated bond is stearin, myristin, palmitin or laurin, water-insoluble cellulose derivative is ethyl cellulose or cellulose acetate, water-insoluble vinyl derivative is polyvinyl acetate or polyvinyl chloride, and water-insoluble acrylic polymer is ethyl acrylate-methyl methacrylate-trimethylammoniumethyl methacrylate chloride copolymer or methyl methacrylate-ethyl acrylate copolymer.

15. Sustained release particles having a mean particle size of 300 $\mu$m or less comprising drug-containing core substance coated with mixed coating of stearic acid-ethyl cellulose.

16. The sustained release particles according to claim 15 wherein, the mixing ratio of stearic acid and ethyl cellulose in the mixed coating of stearic acid-ethyl cellulose is within 5:95 to 95:5.

17. The sustained release particles according to claim 15 wherein, the coating rate of mixed coating of stearic acid-ethyl cellulose is within the range of 20 to 200 wt %.

18. The sustained release particles according to claim 15, that are raw material particles for tablets.

* * * * *